United States Patent
Kühn et al.

(10) Patent No.: US 7,655,706 B2
(45) Date of Patent: *Feb. 2, 2010

(54) POLYMETHYLMETHACRYLATE BONE CEMENT

(75) Inventors: Klaus-Dieter Kühn, Marburg (DE); Sebastian Vogt, Erfurt (DE)

(73) Assignee: Heraeus Kulzer GmhH, Hanau (DE)

( * ) Notice: Subject to any disclaimer, the term of this patent is extended or adjusted under 35 U.S.C. 154(b) by 134 days.

This patent is subject to a terminal disclaimer.

(21) Appl. No.: 11/447,807

(22) Filed: Jun. 6, 2006

(65) Prior Publication Data

US 2006/0293407 A1    Dec. 28, 2006

(30) Foreign Application Priority Data

Jun. 22, 2005  (DE) ........................ 10 2005 029 218
Jul. 13, 2005   (DE) ........................ 10 2005 033 210

(51) Int. Cl.
  *A61F 2/28* (2006.01)
(52) U.S. Cl. .................... 523/112; 523/115; 523/117
(58) Field of Classification Search ................ 523/112, 523/115
  See application file for complete search history.

(56) References Cited

U.S. PATENT DOCUMENTS

| 4,373,217 | A | * | 2/1983 | Draenert ................. 623/23.62 |
|---|---|---|---|---|
| 4,588,583 | A | * | 5/1986 | Pietsch et al. ............... 523/116 |
| 5,258,420 | A | * | 11/1993 | Posey-Dowty et al. ...... 523/116 |
| 6,680,308 | B1 | * | 1/2004 | Hassan ....................... 514/125 |
| 6,743,438 | B2 | * | 6/2004 | Thakrar et al. .............. 424/427 |
| 2006/0062825 | A1 | * | 3/2006 | Maccecchini ............... 424/423 |
| 2007/0031469 | A1 | * | 2/2007 | Kuhn et al. ................. 424/423 |

* cited by examiner

*Primary Examiner*—Tae H Yoon
(74) *Attorney, Agent, or Firm*—Norris McLaughlin & Marcus

(57) ABSTRACT

A polymethylmethacrylate bone cement with a liquid monomer component and a solid component contains in the monomer liquid, for example, 0.001-1.00 mass percent of a dye or dye mixture that is insoluble or poorly soluble in methacrylic acid methylester and, for example, 0.001-2.00 mass percent of a synthetically produced, protein-free, hydrophobic, low molecular or oligomeric solubilizer for the dye or dye mixture. The solubilizer preferably is liquid or pasty at room temperature. The monomer liquid is translucent at room temperature. Preferably, 0.001-1.00 mass percent of a dye or dye mixture that is insoluble or poorly soluble in methacrylic acid methylester and, preferably, 0.001-2.00 mass percent of a synthetically produced, protein-free, hydrophobic, low molecular or oligomeric solubilizer that is liquid or pasty at room temperature are homogeneously dissolved in the polymethacrylate or polymethylacrylate of the powder component.

9 Claims, No Drawings

POLYMETHYLMETHACRYLATE BONE CEMENT

BACKGROUND OF THE INVENTION

Polymethylmethacrylate bone cements (PMMA bone cements) have been in broad use in medicine for decades for anchoring endoprostheses in bone (Klaus-Dieter Kühn: Knochen-zemente für die Endoprothetik: ein aktueller Vergleich der physikalischen und chemischen Eigenschaften handelsüblicher PMMA-Zemente. Springer Verlag Berlin Heidelberg New York, 2001). In general, polymethylmethacrylate bone cements are made up of a liquid monomer component and a powder component. The liquid monomer component consists of methyl-methacrylate and an activator. N,N-dimethyl-p-toluidine is preferably used as activator. The powder component consists of polymethylmethacrylate or polymethyl-co-acrylmethacrylate, an X-ray contrast agent, and a radical initiator. Zirconium dioxide and barium sulfate are customary X-ray contrast agents. Dibenzoylperoxide is preferably used as radical initiator. After mixing the monomer component and powder component, the bone cement hardens within a few minutes by radical polymerization of the monomer.

After mixing, customary polymethylmethacrylate bone cements are provided in the form of white to pale-yellow pasty masses. This occasionally makes a visual differentiation between bone cement and bone tissue difficult. However, it is desirable to be able to distinguish the bone cement from the surrounding bone tissue without any difficulty. For this reason, Heraeus Kulzer has dyed its PMMA bone cements green with chlorophyll for the past approx. 30 years. However, chlorophyll is only very poorly soluble in the methylmethacrylate monomer used in this context. For this reason, refined peanut oil is added to improve the solubility. The refined peanut oil is free of proteins. However, as with any complex natural product, variations of composition are a problem. No alternatives to refined peanut oil have been identified thus far.

Regarding the dyeing of PMMA bone cements, not only the toxicological non-objectionability of the dye, but also the homogeneous distribution of the dye throughout the cement is important. For this reason, bone cements containing dye pigments in their monomer liquid or powder component have not been widely used thus far. In principle, dye pigments are associated with the risk of the dye pigments being released and migrating from the cement matrix. For this reason, it is particularly important for the dye to be distributed homogeneously in the bone cement and firmly enclosed therein.

It is therefore the object of the invention to develop a dyed PMMA bone cement. The liquid monomer component of the PMMA bone cement shall not contain any complex natural products as solubilizer for dyes that are insoluble or only poorly soluble in methylmethacrylate. The liquid monomer component shall contain a homogeneously distributed dye that is dissolved such as to be translucent.

SUMMARY OF THE INVENTION

The object of the invention is met by a bone cement according to claim 1. Preferably, 0.001-1.00 mass percent of a dye or dye mixture that is insoluble or poorly soluble in methacrylic acid methyl ester and 0.001-2.00 mass percent of a synthetically produced, protein-free, hydrophobic, low-molecular or oligomeric solubilizer for the dye or dye mixture are dissolved in the monomer liquid.

DETAILED DESCRIPTION

The monomer liquid is translucent at room temperature.

Preferably, 0.001-1.00 mass percent of a dye or dye mixture that is insoluble or poorly soluble in methacrylic acid methyl ester and 0.001-2.00 mass percent of a synthetically produced, protein-free, hydrophobic, low-molecular or oligomeric solubilizer that is liquid or pasty at room temperature are homogeneously dissolved in the polymethacrylate or polymethylacrylate of the powder component.

In this context, the invention also encompasses the use of copolymers produced by polymerization of acrylic acid esters and/or methacrylic acid esters and styrene or styrene derivatives. Bone cements according to the invention can, in addition, contain agents such as antibiotics—or be free of such agents.

It is also feasible to use two synthetically produced, protein-free, hydrophobic, low molecular or oligomeric solubilizers in order to be able to dissolve a dye in the monomer liquid.

It is useful for the dye/dye mixture and the synthetically produced, protein-free, hydrophobic, low molecular or oligomeric solubilizer to form soluble adducts with the dye/dye mixture in the monomer liquid. Also included in the scope of the invention is adduct formation based on non-polar interactions and the formation of adducts by addition of amino groups or thiol groups to double bonds in terms of a Michael addition is particularly. Also included in the scope of the invention is the formation of adducts by covalent linking by means of the formation of carbonic acid amides, carbonic acid esters, ethers, azomethines, and chelates.

In addition, it is useful that oleic acid esters and/or elaidic acid esters and/or linoleic acid esters and/or linolenic acid esters of the aliphatic alcohols with 1 to 22 carbon atoms or oligomers of these oleic acid esters are preferred as solubilizer.

It is useful that methacrylic acid esters or acrylic acid esters of the aliphatic alcohols with 4 to 16 carbon atoms or oligomers of these methacrylic acid esters with a molecular mass of less than 3,000 g/mol are preferred as solubilizers. Also included in the scope of the invention is the use of maleic acid esters, fumaric acid esters, itaconic acid esters, and sorbic acid esters as solubilizer.

Furthermore, it is useful that glycerine trioleate, glycerine trilinolate, glycerine trilinolenate, and glycerine trielaidinate are preferred as solubilizer. Also included in the scope of the invention is the use of mixed glycerine esters of these unsaturated fatty acids.

It is also useful for the solubilizer to contain double bonds that can be polymerized by radical reaction. One or more double bonds can be present in the solubilizer. The particular advantage is that the solubilizer participates in the radical polymerization of the methylmethacrylate during the hardening of the PMMA bone cement and thus is incorporated into the polymer chains thus generated. This effectively precludes any migration of the solubilizer from the cured PMMA bone cement.

Preferred dyes are chlorophyll, indigo, malachite green, crystal violet, copper phthalocyanine, cobalt phthalocyanine, vitamin B12, and derivatives thereof. Other green, blue, violet or red dyes approved for use in medicine can be used as well. Particularly preferred is the use of chlorophyllin (E141), Brilliant green BS (E142), and Brilliant blue (E133). The invention is illustrated by the following examples, however, without limiting the scope of the invention.

EXAMPLE 1

A total of 1.00 g copper chlorophyllin (dye E141) and 1.00 g oleic acid ethyl ester (Ph. Eur., Fluka) and 18.00 g methylmethacrylate (Fluka) are mixed under stirring for 10 minutes in a 100 ml Erlenmeyer flask. This produces a dark green, clear solution. Then, 980 g methylmethacrylate are added to this solution. This produces a translucent solution that is strongly green in color. The solution is then transferred to 20 ml vials and the vials are sealed by melting. The vials are provided to serve as monomer component for a PMMA bone cement.

EXAMPLE 2

Dibenzoylperoxide was added to a green methylmethacrylate solution prepared according to Example 1, and polymerized at 60° C. in water under vigorous stirring to form polymer beads. The beaded polymer thus produced is then mixed with 30.0 mass percent zirconium dioxide and 1.0 mass percent dibenzoylperoxide and provided as powder component for a PMMA bone cement.

We claim:

1. Polymethylmethacrylate bone cement comprising a liquid monomer component comprising methylmethacrylate and a powder component comprising polymethylmethacrylate, wherein
   A a dye/dye mixture that is insoluble or poorly soluble in methacrylic acid methylester and a synthetically produced, protein-free, hydrophobic, low molecular or oligomeric solubilizer for the dye or dye mixture are dissolved in the monomer liquid;
   B the monomer liquid, with said dye/dye mixture and solubilizer dissolved therein, is translucent at room temperature;
   C and a dye/dye mixture that is insoluble or poorly soluble in methacrylic acid methylester and a synthetically produced, protein-free, hydrophobic, low molecular or oligomeric solubilizer are homogeneously distributed in the polymethylmethacrylate of the powder component.

2. Polymethylmethacrylate bone cement according to claim 1, whereby the dye/dye mixture is present at a concentration of 0.001-1.00 mass percent and the solubilizer is present at a concentration of 0.001-2.00 mass percent in the monomer liquid or, respectively, in the polymethylmethacrylate.

3. Polymethylmethacrylate bone cement according to claim 1, whereby the solubilizer is liquid or pasty at room temperature.

4. Polymethylmethacrylate bone cement comprising a liquid monomer component and a powder component according to claim 1, wherein the dye/dye mixture and the synthetically produced, protein-free, hydrophobic, low molecular or oligomeric solubilizer form soluble adducts with the dye/dye mixture in the monomer liquid.

5. Polymethylmethacrylate bone cement comprising a liquid monomer component and a powder component according to claim 1, wherein oleic acid esters and/or elaidic acid esters and/or linoleic acid esters and/or linolenic acid esters of the aliphatic alcohols with 1 to 22 carbon atoms or oligomers of these oleic acid esters are used as solubilizer.

6. Polymethylmethacrylate bone cement comprising a liquid monomer component and a powder component according to claim 1, wherein methacrylic acid esters or acrylic acid esters of the aliphatic alcohols with 4 to 16 carbon atoms or oligomers of these methacrylic acid esters or acrylic acid esters with a molecular mass of less than 3,000 g/mol are used as solubilizers.

7. Polymethylmethacrylate bone cement comprising a liquid monomer component and a powder component according to claim 1, wherein one or more of glycerine trioleate, glycerine trilinolate, glycerine trilinolenate, and glycerine trielaidinate are used as solubilizer.

8. Polymethylmethacrylate bone cement comprising a liquid monomer component and a powder component according to claim 1, wherein the solubilizer contains double bonds that can be polymerized by radical reaction.

9. Polymethylmethacrylate bone cement comprising a liquid monomer component and a powder component according to claim 1, wherein one or more of chlorophyllin, indigo, malachite green, crystal violet, copper phthalocyanine, cobalt phthalocyanine, and vitamin B12 are used as dyes.

* * * * *